(12) United States Patent
Ishibashi et al.

(10) Patent No.: US 10,524,468 B2
(45) Date of Patent: Jan. 7, 2020

(54) MICROCAPSULE SUSPENSION

(71) Applicant: ISHIHARA SANGYO KAISHA, LTD., Osaka (JP)

(72) Inventors: Yutaka Ishibashi, Osaka (JP); Yusuke Takigami, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 15/574,996

(22) PCT Filed: May 20, 2016

(86) PCT No.: PCT/JP2016/064995
§ 371 (c)(1),
(2) Date: Nov. 17, 2017

(87) PCT Pub. No.: WO2016/186198
PCT Pub. Date: Nov. 24, 2016

(65) Prior Publication Data
US 2018/0139956 A1    May 24, 2018

(30) Foreign Application Priority Data

May 20, 2015   (JP) ................................ 2015-102572

(51) Int. Cl.
| A01N 25/04 | (2006.01) |
| A01N 25/28 | (2006.01) |
| A01N 43/50 | (2006.01) |
| A01N 47/12 | (2006.01) |
| A01N 47/36 | (2006.01) |

(52) U.S. Cl.
CPC ............. *A01N 25/04* (2013.01); *A01N 25/28* (2013.01); *A01N 43/50* (2013.01); *A01N 47/12* (2013.01); *A01N 47/36* (2013.01)

(58) Field of Classification Search
CPC ............................... A01N 25/28; A01N 25/04
See application file for complete search history.

(56) References Cited

U.S. PATENT DOCUMENTS

| 4,376,113 A * | 3/1983 | Suglia .................... A01N 25/28 424/494 |
| 4,394,287 A | 7/1983 | Scarpelli |
| 6,074,986 A | 6/2000 | Mulqueen et al. |
| 2007/0196411 A1 | 8/2007 | Baba et al. |
| 2008/0207445 A1* | 8/2008 | Dexter .................. A01N 25/28 504/100 |
| 2010/0093539 A1 | 4/2010 | Ishihara et al. |
| 2012/0156303 A1 | 6/2012 | Tsuda et al. |

FOREIGN PATENT DOCUMENTS

| EP | 0025379 A2 | 3/1981 |
| GB | 1483542 A | 8/1977 |
| JP | 49-444 A | 1/1974 |
| JP | 51-13386 A | 2/1976 |
| JP | 57-35502 A | 2/1982 |
| JP | 9-510180 A | 10/1997 |
| JP | 2007-153870 A | 6/2007 |
| JP | 2011-57613 A | 3/2011 |
| JP | 2012-25679 A | 2/2012 |
| WO | 95/07614 A1 | 3/1995 |
| WO | 02/089578 A1 | 11/2002 |
| WO | 03/055315 A1 | 7/2003 |
| WO | 2014/169778 A1 | 10/2014 |

OTHER PUBLICATIONS

International Search Report dated Aug. 16, 2016, by the International Searching Authority in counterpart International Application No. PCT/JP2016/064995 (PCT/ISA/210).
Written Opinion dated Aug. 16, 2016 by the International Searching Authority in counterpart International Application No. PCT/JP2016/064995 (PCT/ISA/237).
Communication dated Oct. 19, 2018, issued by the European Patent Office in counterpart European Patent Application No. 16796591.2.

* cited by examiner

*Primary Examiner* — Johann R Richter
*Assistant Examiner* — Danielle Sullivan
(74) *Attorney, Agent, or Firm* — Sughrue Mion, PLLC

(57) ABSTRACT

The present invention relates to a microcapsule suspension containing (1) an oil core compound having a pesticide active agent dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster.

13 Claims, No Drawings

MICROCAPSULE SUSPENSION

TECHNICAL FIELD

The present invention relates to a microcapsule suspension containing a pesticide active agent.

BACKGROUND ART

For controlled release of a pesticide active agent, microencapsulation of the agent is widely known. Moreover, in addition to the controlled release of a pesticide active agent, it is also known to achieve its storage stabilization in microcapsules. For example, Patent Literature 1 describes a storage-stable microcapsule suspension wherein a hydrolysis-sensitive plant treatment agent is covered with a film by coacervation using gelatin and an anionic polymer such as gum arabic and the film is pre-cured with a tanning agent and further cured using a carbonyl compound. It is described that the microcapsules subjected to such treatments achieve both of storage stability and controlled release. Furthermore, Patent Literature 2 describes that highly practical microcapsules, for example, having a thick and strong wall, can be provided by adding a synthetic polymer as a third component since an accumulating quantity of a capsule wall is small and the wall has porous nature in the case where capsulation is performed by causing complex coacervation using only two kinds of wall materials of gelatin and gum arabic.

On the other hand, it has been attempted to prepare a stabilized formulation of a pesticide active agent that is susceptible to hydrolysis, particularly an aqueous formulation whose needs are high in market. For example, Patent Literature 3 describes an aqueous suspended herbicidal composition containing (1) herbicidal sulfonylurea-based compound, (2) an inorganic salt, (3) at least one sulfonate selected from the group consisting of arylsulfonate, alkylarylsulfonate, and their formalin condensates, and (4) water.

CITED REFERENCES

Patent Literatures

Patent Literature 1: JP-A-57-35502
Patent Literature 2: JP-A-51-13386
Patent Literature 3: JP-A-2007-153870

DISCLOSURE OF THE INVENTION

Problems to be Solved by the Invention

In order to prepare a pesticide active agent susceptible to hydrolysis or acid as an aqueous formulation whose market needs are high, it may be possible to consider that the contact with water and acidic substances is avoided as far as possible by microencapsulation of the pesticide active agent. However, by the conventionally known method for strengthening the capsule wall for achieving both of stabilization and controlled release of the pesticide active agent, even if the stabilization of the pesticide active agent is achieved, the pesticide active agent is not quickly released at suitable timing and thus inherent bioactivity cannot be sufficiently exhibited in some cases. On the other hand, it is difficult to prepare an aqueous formulation containing a stabilized pesticide active agent in the first place unless microcapsules that cut the contact between the pesticide active agent susceptible to hydrolysis or acid and water or acidic substances can be prepared. In order to provide a formulation that has a formulation type meeting the needs of the market and has practicality, it is desired to create an aqueous formulation which achieves both of the stabilization of the pesticide active agent susceptible to hydrolysis or acid and sufficient exhibition of the physiological activity. However, for such two problems, a method for solving them utilizing microcapsules has not been known heretofore.

Means for Solving the Problems

When microcapsules are prepared by conventional complex coacervation using gelatin and gum arabic, the capsule wall has porous nature, for example, so that the contact of a pesticide active agent with water or acidic substances is not sufficiently avoided and thus insufficient results are obtained in view of securing the stability of the pesticide active agent susceptible to hydrolysis or acid. According to the prior art, it is attempted to avoid the contact with water or acidic substances by curing the capsule wall. However, when a strong capsule wall is formed, the pesticide active agent is not quickly released and its inherent bioactivity is not sufficiently exhibited in some cases. The present inventors have performed microencapsulation of the pesticide active agent after dispersing it in an oil compound and have achieved both of chemical stabilization of the pesticide active agent and sufficient exhibition of the inherent bioactivity through quick release thereof at suitable timing, and thus they have accomplished the present invention.

That is, the present invention relates to a microcapsule suspension containing (1) an oil core compound having a pesticide active agent dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster. Moreover, the present invention relates to a microcapsule suspension obtained by covering an oil core compound having a pesticide active agent dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate and by suspending it in water, and a production method thereof.

Effect of the Invention

In the microcapsule suspension of the present invention, the pesticide active agent is chemically stabilized at the scene of storing it. At the scene of applying it, the pesticide active agent is quickly released at suitable timing, for example, through breaking of the capsules by the action of shear force at the time of stirring in a spray tank or spray pressure at the time of spraying, and thus the inherent bioactivity can be sufficiently exhibited.

EMBODIMENTS FOR CARRYING OUT THE INVENTION

In the present invention, the microcapsule suspension refers to one where an oil core compound having a dispersed pesticide active agent forms particles covered with a film of a polymer compound formed with a polycationic colloid and a polyanionic colloid utilizing electrostatic interaction between them and the particles are suspended in water. In the present invention, the particles are called microcapsules.

Moreover, it is called microencapsulation to cover the oil core compound containing a pesticide active agent dispersed therein with a film of a polymer compound formed with a polycationic colloid and a polyanionic colloid utilizing electrostatic interaction between them.

In the present invention, the pesticide active agent is used in a state that it is dispersed in an oil compound. At that time, the state may be a state that the whole amount of the blended pesticide active agent is dispersed in the oil compound or may be a state that a part of the blended pesticide active agent is dissolved in the oil compound and the remainder is dispersed therein. In the present invention, a pesticide active agent insoluble in the oil compound is suitably used. However, as mentioned above, a part thereof may be dissolved in the oil compound and thus many of known pesticide active agents are applied. When the pesticide active agent is completely dissolved in the oil compound, as compared with the case where it is not completely dissolved, for example, oxidation of the oil compound and water in the oil compound may more strongly influence the agent and decomposition of the pesticide active agent is accelerated in some cases.

As the pesticide active agents to be applied to the present invention, there may be mentioned active agents such as various herbicides, fungicides, insecticides, and nematicides listed in The Pesticide Manual Sixteenth Edition. With regard to applicable pesticide active agents, one skilled in the art can appropriately select based on the aforementioned requirements and some examples may be mentioned. However, the pesticide active agents applicable to the present invention should not be construed as being limited thereto. Herbicides include sulfonylurea-based compounds such as nicosulfuron, flazasulfuron, and flucetosulfuron. Fungicides include imidazole-based compounds such as cyazofamid. Of these, nicosulfuron is suitably used in the present invention as the pesticide active agent.

In the present invention, the oil compound that disperses the pesticide active agent therein is not particularly limited and, for example, vegetable oils (including methylated seed oils), mineral oils, and the like may be mentioned. Specific examples thereof may be mentioned and the oil compounds to be applied to the present invention should not be construed as being limited thereto. The vegetable oils include olive oil, kapok oil, castor oil, palm oil, camellia oil, coconut oil, sesame oil, corn oil, rice bran oil, peanut oil, cottonseed oil, soybean oil, rapeseed oil, linseed oil, methylated rapeseed oil, rapeseed sirasimeyu (refined oil), and the like. The mineral oils include tung oil, aliphatic hydrocarbon-based solvents, aromatic hydrocarbon-based solvents, and the like.

The microcapsules in the present invention are formed by covering the oil core compound having a dispersed pesticide active agent with a film of a polymer compound formed with a polycationic colloid and a polyanionic colloid utilizing electrostatic interaction between them. That is, it is a method of forming microcapsules by so-called complex coacervation using a polycationic colloid and a polyanionic colloid that are two or more polymer compounds having different charges (causing interaction between positive and negative), and the polycationic colloid and the polyanionic colloid to be materials for the formation can be appropriately selected by one skilled in the art. Some examples may be mentioned and the polycationic colloids and the polyanionic colloids to be applied to the present invention should not be construed as being limited thereto. The polycationic colloids include gelatin, casein, polyamino acids, gelatin derivatives, albumin, hemoglobin, soluble collagen, and the like. Of these, gelatin is preferred as the polycationic colloid. The polyanionic colloids include gum arabic, chitosan, sodium alginate, carrageenan, tragacanth gum, carboxymethyl cellulose, agar, polyvinylbenzenesulfonic acid, polyvinyl methyl ether-maleic anhydride copolymer, surfactants, polyvinyl alcohol, dextrin, crystalline cellulose, carboxyvinyl polymers, and the like. Of these, gum arabic is preferred as the polyanionic colloid.

At the time of preparing the microcapsule suspension of the present invention, the polycationic colloid and the polyanionic colloid are used as aqueous solutions, and with regard to the blending ratio in the aqueous solutions, the polycationic colloid is from 0.02 to 1% by weight, desirably from 0.02 to 0.7% by weight, further desirably from 0.02 to 0.5% by weight, and the polyanionic colloid is from 0.02 to 2% by weight, desirably from 0.02 to 1.4% by weight, further desirably from 0.02 to 1.0% by weight. The mixing ratio of the polycationic colloid and the polyanionic colloid is appropriately adjusted depending on the kinds thereof and the kinds of the other components. The ratio is about from 1:0.02 to 1:100, desirably about from 1:0.02 to 1:75 in a weight ratio.

The pH adjuster in the present invention is one for adjusting the charge of the above polymer compound. Some examples may be mentioned, and the pH adjusters to be applied to the present invention should not be construed as being limited thereto. The pH adjusters include phosphoric acid, hydrochloric acid, boric acid, and the like. The microcapsule suspension of the present invention is adjusted so that pH becomes usually from 1.0 to 4.5, desirably from 2.5 to 3.5.

The microcapsule suspension of the present invention can further contain, in addition to the aforementioned pesticide active agents, the other pesticide active agents and fertilizers. The use in combination of two or more pesticide active agents is usually performed in this field and some advantages, such as extension of the range of weeds, diseases and pests to be controlling targets and achievement of prolongation of terms for exhibiting bioactivity, can be expected. In the present invention, the other pesticide active agents may be encapsulated in the microcapsules or may be contained in the suspension without encapsulation. Some examples thereof may be mentioned, and the other pesticide active agents usable in the present invention should not be construed as being limited thereto.

The following may be mentioned as active agent compounds of herbicides.

(1) Compounds which exhibit herbicidal activity by disturbing hormone action of plants, for example, phenoxy-based compounds such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, 2,4-D choline salt, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide, clomeprop and HIA-1; aromatic carboxylic acid-based compounds such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium, aminopyralid, aminocyclopyrachlor, halauxifen, halauxifen-methyl, and DAS-534; and, in addition, naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl, clacyfos, and the like.

(2) Compounds which exhibit herbicidal activity by inhibiting photosynthesis of plants, for example, urea-based compounds such as chlorotoluron, diuron, fluometuron, linuron, isoproturon, metobenzuron, tebuthiuron, dimefuron, isouron, karbutilate, methabenzthiazuron, metoxuron, metoburomuron, monolinuron, neburon, siduron, terbumeton, and trietazine; triazine-based compounds such as simazine, atrazine, atratone, simetryn, prometryn, dimethametryn, hexazinone, metribuzin, terbuthylazine, cyanazine, ametryn, cybutryne, terbutryn, propazine, metamitron, and prometon; uracil-based compounds such as bromacil, bromacyl-lithium, lenacil, and terbacil; anilide-based compounds such as propanil and cypromid; carbamate-based compounds such as swep, desmedipham, and phenmedipham; hydroxybenzonitrile-based compounds such as bromoxynil, bromoxynil-octanoate, bromoxynil-heptanoate, ioxynil, ioxynil-octanoate, ioxynil-potassium, and ioxynil-sodium; and, in addition, pyridate, bentazone, bentazone-sodium, amicarbazone, methazole, pentanochlor, phenmedipham, and the like.

(3) Quaternary ammonium salt-based compounds which themselves be converted to free radicals in plant bodies and exhibit quick herbicidal activity by generating active oxygen, such as paraquat and diquat.

(4) Compounds which exhibit herbicidal activity by inhibiting chlorophyll biosynthesis of plants and abnormally accumulating photosensitized peroxide substances in plant bodies, for example, diphenyl ether-based compounds such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl, and fluoroglycofen; cyclic imide-based compounds such as chlorphthalim, flumioxazin, flumiclorac, flumiclorac-pentyl, cinidon-ethyl, fluthiacet-methyl, and EK-5385; and, in addition, oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, fluazolate, profluazol, flufenpyr-ethyl, bencarbazone, tiafenacil, pyrachlonil, trifludimoxazin, HNPC-B4047, IR-6396, EK-5439, EK-5498, SYN-523, compounds described in WO2008/008763 (FMC), and the like.

(5) Compounds which exhibit herbicidal activity whose characteristic is bleaching effect, by inhibiting chromogenesis of plants such as carotenoids, for example, pyridazinone-based compounds such as norflurazon, chloridazon, and metflurazon; pyrazole-based compounds such as pyrazolynate, pyrazoxyfen, benzofenap, topramezone, pyrasulfotole, and tolpyralate; and, in addition, amitrole, fluridone, flurtamone, diflufenican, methoxyphenone, clomazone, sulcotrione, mesotrione, tembotrione, tefuryltrione, fenquinotrione, cyclopyrimorate, isoxaflutole, difenzoquat, difenzoquat-metilsulfate, isoxachlortole, benzobicyclon, bicyclopyron, picolinafen, beflubutamid, ketospiradox, ketospiradox-potassium, and the like.

(6) Compounds which exhibit herbicidal activity on plants by inhibiting biosynthesis of fatty acids, for example, aryloxyphenoxypropionic acid-based compounds such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop, propaquizafop, HNPC-A8169, and SYP-1924; cyclohexanedione-based compounds such as alloxydim-sodium, alloxydim, clethodim, sethoxydim, tralkoxydim, butroxydim, tepraloxydim, profoxydim, and cycloxydim; phenylpyrazoline-based compounds such as pinoxaden; and the like.

(7) Compounds which exhibit herbicidal activity by inhibiting amino acid biosynthesis of plants, for example, sulfonylurea compounds such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, flucetosulfuron, cyclosulfamuron, prosulfuron, flupyrsulfuron-methyl-sodium, flupyrsulfuron, triflusulfuron-methyl, triflusulfuron, halo sulfuron-methyl, halo sulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, amidosulfuron, azimsulfuron, propyrisulfuron, metazosulfuron, methiopyrsulfuron, monosulfuron-methyl, orsosulfuron, iofensulfuron, and iofensulfuron-sodium; triazolopyrimidinesulfonamide-based compounds such as flumetsulam, metosulam, diclosulam, cloransulam-methyl, florasulam, penoxsulam, and pyroxsulam; imidazolinone-based compounds such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl, and imazapic; pyrimidylsalicylic acid-based compounds such as pyrithiobac-sodium, bispyribac-sodium, pyriminobac-methyl, pyribenzoxim, pyriftalid, pyrimisulfan, and triafamone; sulfonylaminocarbonyltriazolinone-based compounds such as flucarbazone, flucarbazone-sodium, propoxycarbazone-sodium, propoxycarbazone, and thiencarbazone-methyl; and, in addition, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin, and the like.

(8) Compounds which exhibit herbicidal activity by inhibiting cell mitosis of plants, for example, dinitroaniline-based compounds such as trifluralin, oryzalin, nitralin, pendimethalin, ethalfluralin, benfluralin, prodiamine, butralin, and dinitramine; amide-based compounds such as bensulide, napropamide, napropamide-M, propyzamide, and pronamide; organophosphorus-based compounds such as amiprofos-methyl, butamifos, anilofos, and piperophos; phenylcarbamate-based compounds such as propham, chlorpropham, barban, and carbetamide; cumylamine-based compounds such as daimuron, cumyluron, bromobutide, and methyldymron; and, in addition, asulam, asulam-sodium, dithiopyr, thiazopyr, chlorthal-dimethyl, chlorthal, diphenamid, flamprop-M-methyl, flamprop-M, flamprop-M-isopropyl, and the like.

(9) Compounds which exhibit herbicidal activity by inhibiting protein biosynthesis or lipid biosynthesis of plants, for example, chloroacetamide-based compounds such as alachlor, metazachlor, butachlor, pretilachlor, metolachlor, S-metolachlor, thenylchlor, pethoxamid, acetochlor, propachlor, dimethenamide, dimethenamide-P, propisochlor, and dimethachlor; thiocarbamate-based compounds such as molinate, dimepiperate, pyributicarb, EPTC, butylate, vernolate, pebulate, cycloate, prosulfocarb, esprocarb, thiobencarb, diallate, tri-allate, and orbencarb; and, in addition, etobenzanid, mefenacet, flufenacet, tridiphane, cafenstrole, fentrazamide, oxaziclomefone, indanofan, benfuresate, pyroxasulfone, fenoxasulfone, methiozolin, dalapon, dalapon-sodium, TCA-sodium, trichloroacetic acid, and the like.

(10) Compounds which exhibit herbicidal activity by inhibiting cellulose biosynthesis of plants, such as dichlobenil, triaziflam, indaziflam, flupoxam, and isoxaben.

(11) Other herbicides such as MSMA, DSMA, CMA, endothall, endothall-dipotassium, endothall-sodium, endothall-mono (N,N-dimethylalkylammonium), ethofumesate, sodium chlorate, pelargonic acid, nonanoic acid, fosamine, fosamine-ammonium, ipfencarbazone, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, xanthinosin, herbimycin, unguinol, metatyrosine, sarmentine, thaxtominA, mevalocidin, alpha-limonene, pyribambenz-propyl, pyribambenz-isopropyl, JS-913, KHG-23844, H-9201, SIOC-0163, SIOC-0171, SIOC-0172, SIOC-0285, SIOC-0426, SIOC-H-057, ZJ-0166, ZJ-1835, ZJ-0453, ZJ-0777, ZJ-0862, and compounds described in WO2008/096398 (Kumiai Chemical Industry Co., Ltd.).

The following may be mentioned as active agent compounds of fungicides.

Anilinopyrimidine-based compounds such as mepanipyrim, pyrimethanil, and cyprodinil;

Triazolopyrimidine-based compounds such as 5-chloro-7-(4-methylpiperidin-1-yl)-6-(2,4,6-trifluorophenyl)[1,2,4]triazolo[1,5-a]pyrimidine;

Pyridinamine-based compounds such as fluazinam;

Azole-based compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, azaconazole, triticonazole, and imazalil;

Quinoxaline-based compounds such as quinomethionate;

Dithiocarbamate-based compounds such as maneb, zineb, mancozeb, polycarbamate, metiram, propineb, and thiram;

Organochlorine-based compounds such as fthalide, chlorothalonil, and quintozene;

Imidazole-based compounds such as benomyl, thiophanate-methyl, carbendazim, thiabendazole, fuberiazole, and cyazofamid;

Cyanoacetamide-based compounds such as cymoxanil;

Anilide-based compounds such as metalaxyl, metalaxyl-M(mefenoxam), oxadixyl, ofurace, benalaxyl, benalaxyl-M (kiralaxyl, chiralaxyl), furalaxyl, cyprofuram, carboxin, oxycarboxin, thifluzamide, boscalid, bixafen, isotianil, tiadinil, and sedaxane;

Sulfamide-based compounds such as dichlofluanid;

Copper-based compounds such as cupric hydroxide and oxine copper;

Isoxazole-based compounds such as hymexazol;

Organophosphorus-based compounds such as fosetyl-Al, tolclofos-Methyl, S-benzyl O,O-diisopropyl phosphorothioate, O-ethyl S,S-diphenyl phosphorodithioate, aluminum ethyl hydrogen phosphonate, edifenphos, and iprobenfos;

Phthalimide-based compounds such as captan, captafol, and folpet;

Dicarboxyimide-based compounds such as procymidone, iprodione, and vinclozolin;

Benzanilide-based compounds such as flutolanil, mepronil, and benodanil;

Amide-based compounds such as penthiopyrad, penflufen, furametpyr, isopyrazam, silthiopham, fenoxanil, fenfuram, fluxapyroxad, and benzovindiflupyr;

Benzamide-based compounds such as fluopyram and zoxamide;

Piperazine-based compounds such as triforine;

Pyridine-based compounds such as pyrifenox and pyrisoxazole;

Carbinol-based compounds such as fenarimol and nuarimol;

Piperidine-based compounds such as fenpropidin;

Morpholine-based compounds such as fenpropimorph and tridemorph;

Organotin-based compounds such as fentin hydroxide and fentin acetate;

Urea-based compounds such as pencycuron;

Cinnamic acid-based compounds such as dimethomorph and flumorph;

Phenylcarbamate-based compounds such as diethofencarb;

Cyanopyrrole-based compounds such as fludioxonil and fenpiclonil;

Strobilurin-based compounds such as azoxystrobin, kresoxim-methyl, metominostrobin, trifloxystrobin, picoxystrobin, oryzastrobin, dimoxystrobin, pyraclostrobin, fluoxastrobin, enestroburin, pyraoxystrobin, pyrametostrobin, coumoxystrobin, enoxastrobin, fenaminstrobin, flufenoxystrobin, triclopyricarb, and mandestrobin;

Oxazolidinone-based compounds such as famoxadone;

Thiazolecarboxamide-based compounds such as ethaboxam;

Valinamide-based compounds such as iprovalicarb and benthiavalicarb-isopropyl; Acylamino acid-based compounds such as methyl N-(isopropoxycarbonyl)-L-valyl-(3RS)-3-(4-chlorophenyl)-β-alaninate (valiphenalate);

Imidazolinone-based compounds such as fenamidone;

Hydroxyanilide-based compounds such as fenhexamid;

Benzenesulfonamide-based compounds such as flusulfamide;

Oxime ether-based compounds such as cyflufenamid;

Anthraquinone-based compounds;

Crotonic acid-based compounds;

Antibiotics such as validamycin, kasugamycin, and polyoxins;

Guanidine-based compounds such as iminoctadine and dodine;

Quinoline-based compounds such as tebufloquin;

Thiazolidine-based compounds such as flutianil;

Sulfur-based compounds such as Sulfur;

As other compounds, there may be mentioned pyribencarb, isoprothiolane, pyroquilon, diclomezine, quinoxyfen, propamocarb hydrochloride, chloropicrin, dazomet, metam-sodium, metrafenone, nicobifen, UBF-307, diclocymet, proquinazid, amisulbrom(amibromdole), mandipropamid, fluopicolide, carpropamid, meptyldinocap, isofetamid, pyriofenone, ferimzone, spiroxamine, fenpyrazamine, ametoctradin, valifenalate, oxathiapiprolin, tolprocarb, picarbutrazox, SB-4303, BAF-1107, SYJ-247, NNF-0721, and the like.

The following may be mentioned as active agent compounds of insecticides, acaricides, nematicides, or soil pesticides.

Organic phosphate ester-based compounds such as profenofos, dichlorvos, fenamiphos, fenitrothion, EPN, diazinon, chlorpyrifos, chlorpyrifos-methyl, acephate, prothiofos, fosthiazate, cadusafos, disulfoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim, and triazophos;

Carbamate-based compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC, and fenothiocarb;

Nereistoxin derivatives such as cartap, thiocyclam, bensultap, thiosultap-sodium, thiosultap-disodium, monosultap, bisultap, and thiocyclam hydrogen oxalate;

Organochlorine-based compounds such as dicofol, tetradifon, endosulfan, dienochlor, and dieldrin;

Organometallic compounds such as fenbutatin oxide and cyhexatin;

Pyrethroid-based compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, flumethrin, and decamethrin;

Benzoylurea-based compounds such as diflubenzuron, chlorfluazuron, teflubenzuron, flufenoxuron, triflumuron, hexaflumuron, lufenuron, novaluron, noviflumuron, bistrifluron, and fluazuron;

Juvenile hormone-like compounds such as methoprene, pyriproxyfen, fenoxycarb, and diofenolan;

Pyridazinone-based compounds such as pyridaben;

Pyrazole-based compounds such as fenpyroximate, fipronil, tebufenpyrad, ethiprole, tolfenpyrad, acetoprole, pyrafluprole, and pyriprole;

Neonicotinoid-based compounds such as imidacloprid, nitenpyram, acetamiprid, thiacloprid, thiamethoxam, clothianidin, nidinotefuran, dinotefuran, and nithiazine;

Hydrazine-based compounds such as tebufenozide, methoxyfenozide, chromafenozide, and halofenozide;

Pyridine-based compounds such as pyridalyl and flonicamid;

Cyclic ketoenol-based compounds such as spirodiclofen, spiromesifen, and spirotetramat;

Strobilurin-based compounds such as fluacrypyrim;

Pyridinamine-based compounds such as flufenerim;

Dinitro-based compounds, organosulfur compounds, urea-based compounds, triazine-based compounds, hydrazone-based compounds, and, as other compounds, there may be mentioned flometoquin, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyclaniliprole, cyenopyrafen, pyrifluquinazon, fenazaquin, amidoflumet, sulfluramid, hydramethylnon, metaldehyde, ryanodine, verbutin, chlorobenzoate, thiazolylcinnanonitrile, sulfoxaflor, fluensulfone, triflumezopyrim, afidopyropen, flupyradifuron, NC-515, tetraniliprole, fluralaner, broflanilide, dicloromezotiaz, fluhexafon, tioxazafen, DKN-2601, MSI-1302, NA-89, and the like.

In the present invention, at the time of preparing the microcapsule suspension, various additives can be used. Some examples may be mentioned and the additives to be applied to the present invention should not be construed as being limited thereto. As for individual agents of these additives, one or two or more thereof can be appropriately selected and used unless they depart from the purpose of the present invention.

The additives include phosphate such as sodium dihydrogen phosphate and potassium dihydrogen phosphate; anionic surfactants such as fatty acid salts, benzoate, alkyl sulfosuccinate, dialkyl sulfosuccinate, polycarboxylate, alkyl sulfate ester salts, alkyl sulfate, alkyl diglycol ether sulfate, alcohol sulfate ester salts, alkyl sulfonate, lignin sulfonate, alkyl diphenyl ether disulfonate, polystyrenesulfonate, alkyl phosphate ester salts, alkylaryl phosphate, styrylaryl phosphate, polyoxyethylene alkyl ether sulfate ester salts, polyoxyethylene alkylaryl ether sulfate, polyoxyethylene styrylaryl ether sulfate, polyoxyethylene styrylaryl ether sulfate ammonium salts, polyoxyethylene alkylaryl ether sulfate ester salts, polyoxyethylene alkyl ether phosphate, polyoxyethylene alkylaryl phosphate ester salts, polyoxyethylene styrylaryl ether phosphate esters or salts thereof, salts of phenolsulfonic acid-formalin condensates, alkyl maleate block polymers, arylsulfonate, alkylarylsulfonate, arylsulfonate-formalin condensates, and alkylarylsulfonate-formalin condensates; non-ionic surfactants such as sorbitan fatty acid esters, glycerin fatty acid esters, fatty acid polyglycerides, fatty acid alcohol polyglycol ethers, acetylene glycol, acetylene alcohol, oxyalkylene block polymers, polyoxyethylene alkyl ethers, polyoxyethylene alkylaryl ethers, polyoxyethylene styrylaryl ethers, polyoxyethylene glycol alkyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene hardened castor oil, polyoxyethylene castor oil, and polyoxypropylene fatty acid ester; cationic surfactants such as alkoxylated fatty amines; polymer-type surfactants such as polyacrylate, polydiallyldimethylammonium chloride, styrene-maleic acid copolymer salts, styrene-maleic acid half ester copolymer salts, carboxymethyl cellulose salts, polyalkylenepolyamine alkylene oxide adducts, polyalkylenepolyimine alkylene oxide adducts, and polyvinylpyrrolidone; anti-settling agents such as silica, organic bentonite (bentonite-alkylamino complex), bentonite, white carbon, and aluminum magnesium silicate; thickeners such as xanthan gum, guar gum, polyvinyl alcohol, carboxymethyl cellulose sodium salt, sodium alginate, bentonite, and white carbon; defoamers such as polydimethylsiloxane and acetylene alcohol; antifreezing agents such as ethylene glycol, propylene glycol, glycerin, and urea; antiseptics such as formalin, parachlorometaxylenol, and 1,2-benzisothiazolin-3-one; solvents such as propanol, isobutanol, ethylene glycol, propylene glycol, diethylene glycol, hexylene glycol, polyethylene glycol, polypropylene glycol, glycerin, propyl cellosolve, butyl cellosolve, phenyl cellosolve, propylene glycol monomethyl ether, propylene glycol monoethyl ether, propylene glycol monopropyl ether, propylene glycol monobutyl ether, propylene glycol monophenyl ether, dioxane, cyclohexanone, methyl isobutyl ketone, acetic acid, butyric acid, isopropyl acetate, butyl acetate, N-methylformamide, N-methylpyrrolidone, dimethylsulfoxide, 1,3-dimethyl-2-imidazolidinone, amines, ether amines, normal paraffins, isoparaffins, alkylbenzenes, alkylnaphthalenes, and phenylxylylethane.

The blending ratio of each component in the microcapsule suspension of the present invention may be appropriately changed depending on the kinds of the blending components, application scenes, and the like and hence cannot be unconditionally specified. For example, the pesticide active agent is from 0.01 to 40 parts by weight, desirably from 1 to 20 parts by weight, the oil compound is from 0.01 to 50 parts by weight, desirably from 5 to 30 parts by weight, the polycationic colloid is from 0.01 to 10 parts by weight, desirably from 0.01 to 0.5 parts by weight, the polyanionic colloid is from 0.01 to 10 parts by weight, desirably from 0.01 to 1 part by weight, the pH adjuster may be appropriately added in such an amount that can achieve adjustment to desired pH, for example, several drops thereof may be added, and the main component of the remainder is water, which is specifically from 40 to 99 parts by weight, desirably from 40 to 93 parts by weight.

In the case where various components are arbitrarily contained in the microcapsule suspension of the present invention, the blending ratio of each component is, for example, as follows. The other pesticide active agent is from 0.01 to 80 parts by weight, desirably from 0.1 to 40 parts by weight, the phosphate is from 1 to 10 parts by weight, desirably from 2 to 8 parts by weight, the surfactant is from 0.01 to 20 parts by weight, desirably from 0.1 to 5 parts by weight, and the thickener is from 0.01 to 5 parts by weight, desirably from 0.05 to 1 part by weight.

The microcapsule suspension of the present invention is prepared, for example, as follows.

1) A pesticide active agent and an oil compound are mixed to prepare an oil core compound (oil slurry) wherein the pesticide active agent is dispersed in the oil compound. The mixing is performed under strong stirring and, for example, a device such as a homogenizer or a paint shaker can be used. In the case where a homogenizer is used for mixing, arbitrary rotation speed can be selected, for example, stirring and mixing can be performed at about 500 to 10,000 rpm. The temperature at mixing is usually 40° C. or higher.

2) A polycationic colloid and a polyanionic colloid are dissolved in water so as to be predetermined contents, thus preparing an aqueous solution, and it is mixed with the oil core compound to form an O/W emulsion. The mixing is performed under strong stirring and, for example, a device such as a homogenizer can be used. In the case where a homogenizer is used for mixing, arbitrary rotation speed can be selected, for example, stirring and mixing can be performed at about from 500 to 10,000 rpm. The operation is conducted at a temperature higher than the temperature at which the polycationic colloid is gelled and the temperature at mixing is usually about from 40 to 70° C. The particle diameter of oil drops in the emulsion is usually from 10 to 100 μm and desirably, it is desired to prepare it so as to be from 40 to 80 μm.

3) A pH adjuster is added to and mixed with the O/W emulsion and the oil core compound is covered with a film of a polymer compound to microencapsulate, thereby preparing the microcapsule suspension of the present invention. The adjustment of pH is performed at a temperature equal to or higher than the temperature at which the polycationic colloid is gelled and the temperature is usually about from 40 to 70° C. After the pH adjustment, the temperature is gradually lowered so that it becomes equal to or lower than the temperature at which the polycationic colloid is gelled, thus completing the microencapsulation. Usually it is suitable to control the temperature to about from 5 to 25° C. The mixing is performed under weak stirring and, as a stirrer, for example, a stirrer with blades can be used. The rotation speed can be arbitrarily selected, for example, stirring and mixing can be performed at about from 50 to 500 rpm.

In the case of blending the other pesticide active agent and various additives, they can be added in any step.

With regard to the microcapsule suspension of the present invention, at the scene of storing it, the pesticide active agent is stabilized. However, at the scene of applying it, the inherent bioactivity can be sufficiently exhibited by applying it using a method usually performed in the art.

The following will describe desirable embodiments in the present invention and the present invention should not be construed as being limited thereto.

[1] A microcapsule suspension containing (1) an oil core compound having nicosulfuron or flazasulfuron dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster.

[2] A microcapsule suspension containing (1) an oil core compound having nicosulfuron dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster.

[3] A microcapsule suspension containing (1) an oil core compound having flazasulfuron dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster.

[4] A microcapsule suspension containing (1) an oil core compound having cyazofamid dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, and (3) a pH adjuster.

[5] A microcapsule suspension containing (1) an oil core compound having cyazofamid dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight, (3) a pH adjuster, and (4) propamocarb hydrochloride.

[6] A microcapsule suspension obtained by covering an oil core compound having nicosulfuron or flazasulfuron dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate and by suspending it in water.

[7] A microcapsule suspension obtained by covering an oil core compound having nicosulfuron dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate and by suspending it in water.

[8] A microcapsule suspension obtained by covering an oil core compound having flazasulfuron dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate and by suspending it in water.

[9] A microcapsule suspension obtained by covering an oil core compound having cyazofamid dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate and by suspending it in water.

[10] A microcapsule suspension obtained by covering an oil core compound having cyazofamid dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight and a pH adjuster to microencapsulate, by suspending it in water, and by including propamocarb hydrochloride in the suspension.

[11] The microcapsule suspension as described in [1] to [10] above, wherein pH is from 1.0 to 4.5.

[12] The microcapsule suspension as described in [1] to [10] above, wherein the oil compound is a vegetable oil or a mineral oil.

[13] The microcapsule suspension as described in [1] to [12] above, wherein the polycationic colloid is at least one selected from the group consisting of gelatin, casein, polyamino acids, gelatin derivatives, albumin, hemoglobin, and soluble collagen and the polyanionic colloid is at least one selected from the group consisting of gum arabic, chitosan, sodium alginate, carrageenan, tragacanth gum, carboxymethyl cellulose, agar, polyvinylbenzenesulfonic acid, polyvinyl methyl ether-maleic anhydride copolymer, surfactants, polyvinyl alcohol, dextrin, crystalline cellulose, carboxyvinyl polymers.

[14] The microcapsule suspension as described in [1] to [12] above, wherein the polycationic colloid is gelatin and the polyanionic colloid is gum arabic.

[15] A production method of a microcapsule suspension, comprising (a) a step of mixing a pesticide active agent and an oil compound to prepare an oil dispersion of the pesticide active agent, (b) a step of preparing an aqueous solution containing a polycationic colloid and a polyanionic colloid in a ratio that the polycationic colloid is from 0.02 to 1% by weight and the polyanionic colloid is from 0.02 to 2% by weight, (c) a step of mixing the oil dispersion and the aqueous solution to form an O/W emulsion, and (d) a step of adding a pH adjuster to the O/W emulsion and mixing them.

[16] A microcapsule suspension containing (1) an oil core compound having a pesticide active agent dispersed in an oil compound, (2) an aqueous solution containing a polycationic colloid and a polyanionic colloid, and (3) a pH adjuster, wherein the blending ratio in the microcapsule suspension is a ratio that the pesticide active agent is from 0.01 to 40 parts by weight, the oil compound is from 0.01 to 50 parts by weight, the polycationic colloid is from 0.01 to 10 parts by weight, the polyanionic colloid is from 0.01 to 10 parts by weight, and water is from 40 to 99 parts by weight.

[17] The microcapsule suspension as described in [16] above, wherein the oil compound is a vegetable oil or a mineral oil and the pesticide active agent is nicosulfuron.

EXAMPLES

In order to mention the present invention in more detail, Examples will be described in the following. First, Formulation Examples will be described.

Formulation Example 1

(1) Using a paint shaker, 30 parts by weight of nicosulfuron (purity 95.1%) and 70 parts by weight of methylated seed oil (trade name: Agunique ME 18 RDF, manufactured by BASF) were pulverized and mixed for 1 hour to obtain an oil slurry.

(2) An aqueous solution (70 parts by weight) containing a gelatin purified powder (0.06% by weight, trade name: gelatin fine powder, manufactured by Nacalai Tesque, the trade name and the manufacturer are the same in the following) and a gum arabic powder (0.12% by weight, trade name: gum arabic, manufactured by Nacalai Tesque, the trade name and the manufacturer are the same in the following) was heated to 60° C. and was added to 30 parts by weight of the oil slurry prepared in the previous step (1) in a hot water bath at 60° C. and the whole was stirred for 5 minutes using a homogenizer to obtain an emulsion.

(3) An aqueous 10% by weight phosphoric acid solution was added to the emulsion prepared in the previous step (2) to adjust pH to 2.8. While stirring the solution with a stirrer, the solution was allowed to stand until the temperature reached room temperature to obtain a microcapsule suspension.

(4) To 91.7 parts by weight of the microcapsule suspension prepared in the previous step (3), 8.3 parts by weight of sodium dihydrogen phosphate was added, and the whole was mixed with a stirrer to obtain a microcapsule suspension.

Formulation Example 2

A microcapsule suspension was obtained in the same manner as in the above Formulation Example 1 except that 70 parts by weight of an aqueous solution containing a gelatin purified powder (0.125% by weight) and a gum arabic powder (0.25% by weight) was used.

Formulation Example 3

A microcapsule suspension was obtained in the same manner as in the above Formulation Example 1 except that 70 parts by weight of an aqueous solution containing a gelatin purified powder (0.25% by weight) and a gum arabic powder (0.5% by weight) was used.

Formulation Example 4

(1) Using a paint shaker, 30 parts by weight of cyazofamid (purity 96.3%) and 70 parts by weight of an aliphatic hydrocarbon-based solvent (trade name: IP-solvent, manufactured by Idemitsu Petrochemical Co., Ltd.) were pulverized and mixed for 1 hour to obtain an oil slurry.

(2) An aqueous solution (70 parts by weight) containing a gelatin purified powder (0.06% by weight) and a gum arabic powder (0.12% by weight) was heated to 60° C. and was added to 30 parts by weight of the oil slurry prepared in the previous step (1) in a hot water bath at 60° C., and the whole was stirred for 5 minutes using a homogenizer to obtain an emulsion.

(3) An aqueous 10% by weight phosphoric acid solution was added to the emulsion prepared in the previous step (2) to adjust pH to 2.8. While stirring the solution with a stirrer, the solution was allowed to stand until the temperature reached room temperature to obtain a microcapsule suspension of cyazofamid. A mixed microcapsule suspension of cyazofamid and propamocarb hydrochloride was obtained by mixing 30 parts by weight of this microcapsule suspension, 56 parts by weight of an aqueous 66.66% by weight propamocarb hydrochloride solution, and 14 parts by weight of water.

Formulation Example 5

A mixed microcapsule suspension was obtained in the same manner as in the above Formulation Example 4 except that 70 parts by weight of an aqueous solution containing a gelatin purified powder (0.125% by weight) and a gum arabic powder (0.25% by weight) was used.

Formulation Example 6

A mixed microcapsule suspension was obtained in the same manner as in the above Formulation Example 4 except that 70 parts by weight of an aqueous solution containing a gelatin purified powder (0.25% by weight) and a gum arabic powder (0.5% by weight) was used.

Formulation Example 7

A microcapsule suspension was obtained in the same manner as in the above Formulation Example 1 except that 70 parts by weight of an aqueous solution containing a gelatin purified powder (0.05% by weight) and a gum arabic powder (0.1% by weight) was used.

Formulation Example 8

A microcapsule suspension was obtained in the same manner as in the above Formulation Example 1 except that 70 parts by weight of an aqueous solution containing a gelatin purified powder (0.025% by weight) and a gum arabic powder (0.05% by weight) was used.

Formulation Example 9

A microcapsule suspension was obtained in the same manner as in the above Formulation Example 1 except that 70 parts by weight of an aqueous solution containing a gelatin purified powder (0.1% by weight) and a gum arabic powder (0.2% by weight) was used.

Formulation Example 10

A microcapsule suspension was obtained in the same manner as in the above Formulation Example 1 except that 70 parts by weight of an aqueous solution containing a gelatin purified powder (0.5% by weight) and a gum arabic powder (1.0% by weight) was used.

Formulation Example 11

A microcapsule suspension was obtained in the same manner as in the above Formulation Example 1 except that the step (2) was carried out at 70° C. in the above Formulation Example 1.

Formulation Example 12

A microcapsule suspension was obtained in the same manner as in the above Formulation Example 1 except that the step (2) was carried out at 50° C. in the above Formulation Example 1.

Formulation Example 13

A microcapsule suspension was obtained by mixing 97 parts by weight of the microcapsule suspension prepared in the same manner as in the above Formulation Example 1 and 3 parts by weight of sorbitan sesquioleate (trade name: SORGEN 30, manufactured by DKS Co., Ltd.) and stirring the whole.

Formulation Example 14

A microcapsule suspension was obtained by mixing 97 parts by weight of the microcapsule suspension prepared in the same manner as in the above Formulation Example 1 and 3 parts by weight of sodium carboxymethyl cellulose (trade name: CELLOGEN A70, manufactured by DKS Co., Ltd.) and stirring the whole.

Formulation Example 15

An aqueous solution containing 5% by weight of aluminum magnesium silicate (trade name: Veegum R, manufactured by Vanderbilt), 2% by weight of benzisothiazolin-3-one (trade name: Proxcel GXL, manufactured by LONZA), and 1.5% by weight of xanthan gum (trade name: Rhodopol 23, manufactured by Solvay) was prepared. A microcapsule suspension was obtained by mixing 20 parts by weight of this aqueous solution and 80 parts by weight of the microcapsule suspension prepared in the same manner as in the above Formulation Example 1.

Comparative Formulation Example 1

An aqueous suspension was obtained by mixing 8.33 parts by weight of nicosulfuron (purity 95.1%), 1.25 parts by weight of sodium salt of naphthalenesulfonic acid-formalin condensate (trade name: Morwet D425, manufactured by Akzo Novel), 2.3 parts by weight of sodium dihydrogen phosphate, 0.083 parts by weight of dimethylpolysiloxane (trade name: Silcolapse 432, manufactured by Bluestar silicones), 0.13 parts by weight of xanthan gum (trade name: Rhodopol 23, manufactured by Solvay), 0.063 parts by weight of benzisothiazolin-3-one (trade name: Proxcel GXL, manufactured by LONZA), and 87.844 parts by weight of water in a paint shaker.

Comparative Formulation Example 2

An aqueous suspension was obtained by mixing 3.18 parts by weight of cyazofamid (purity 96.3%), 56.39 parts by weight of an aqueous 66.66% by weight propamocarb hydrochloride solution, 1 part by weight of tristyrylphenyl ethoxylate (trade name: Soprophor FLK/70, manufactured by Solvay), 0.5 parts by weight of aluminum silicate (trade name: Veegum R, manufactured by Van derbilt), 0.1 parts by weight of a silicone defoamer (trade name: Silfoam SE-47, manufactured by Wacker Asahikasei silicone Co., Ltd.), 0.15 parts by weight of xanthan gum (trade name: Rhodopol 23, manufactured by Solvay), 0.1 parts by weight of benzisothiazolin-3-one (trade name: Proxcel GXL, manufactured by LONZA), and 38.58 parts by weight of water.

Comparative Formulation Example 3

A microcapsule suspension was obtained in the same manner as in the above Formulation Example 1 except that 70 parts by weight of an aqueous solution containing a gelatin purified powder (0.001% by weight) and a gum arabic powder (0.00025% by weight) was used.

Comparative Formulation Example 4

A microcapsule suspension was obtained in the same manner as in the above Formulation Example 1 except that 70 parts by weight of an aqueous solution containing a gelatin purified powder (1.5% by weight) and a gum arabic powder (3.0% by weight) was used.

Comparative Formulation Example 5

A microcapsule suspension was obtained in the same manner as in the above Formulation Example 1 except that 70 parts by weight of an aqueous solution containing a gelatin purified powder (2.0% by weight) and a gum arabic powder (4.0% by weight) was used.

The following will describe Test Examples.

Test Example 1

Each of the microcapsule suspensions prepared in the above Formulation Examples 1 to 6 was placed in an amount of 20 ml each in a sample bottle having a volume of 30 ml and was stored in an incubator at 54° C. for 2 weeks. Thereafter, its appearance was observed on a microscope. As a result, the structures of the microcapsules were maintained in all the Formulation Examples.

Test Example 2

Each of the microcapsule suspensions prepared in the above Formulation Examples 1 to 6 and Comparative Formulation Examples 1 and 2 was stored in an incubator at 54° C. for 2 weeks. The content of the pesticide active agent before and after the time passage was quantitatively determined by liquid chromatography, the decomposition rate thereof was calculated according to the following expression, and thereby the change with time was evaluated. The results are shown in Table 1.

Decomposition rate (%)=[(Content immediately after production−Content after storage)/Content immediately after production]×100

TABLE 1

| Pesticide active agent | Suspension | Decomposition rate (%) |
| --- | --- | --- |
| Nicosulfuron | Formulation Example 1 | 0.98 |
| | Formulation Example 2 | 0.23 |
| | Formulation Example 3 | −0.60 |
| | Comparative Formulation Example 1 | 50.51 |
| Cyazofamid | Formulation Example 4 | −1.66 |
| | Formulation Example 5 | −1.38 |
| | Formulation Example 6 | 2.74 |
| | Comparative Formulation Example 2 | 25.00 |

The microcapsule suspensions of the present invention exhibit improved storage stability of the pesticide active agent as compared with conventional aqueous suspensions.

Test Example 3

A pot of 1/1,000,000 ha was filled with upland farming soil and seeds of crabgrass (*Digitaria ciliaris* (Retz.) Koel) were sown thereon. When crabgrass reached 5-leaves stage, a predetermined amount of each of the microcapsule suspensions prepared in the above Formulation Examples 1 to 3 was diluted with water containing 0.5% by volume of an agricultural adjuvant (trade name: Destiny HC, manufactured by WINFIELD SOLUTIONS LCC) (corresponding to 300 liters per 1 ha) and foliage treatment was performed using a full automatic spaying apparatus (equipped with Teejet 80015VS nozzle manufactured by Teejet, pressure=40 psi).

After the treatment with the agent, the state of growth of the crabgrass was visually observed on the 21st day. The results of evaluation according to the following evaluation criteria are shown in Table 2.

Growth inhibition rate (%)=Weed inhibition rate (%) of 0(equivalent to non-treated pot) to 100(complete kill)

TABLE 2

| Formulation Example | Amount of pesticide active agent (g/ha) | Growth inhibition rate of crabgrass (%) |
| --- | --- | --- |
| 1 | 30 | 81 |
| 2 | 30 | 75 |
| 3 | 30 | 80 |

Test Example 4

A tomato (variety: Sekai-ichi) was cultivated in a plastic pot having a diameter of 7.5 cm. When it reached 3-leaves stage, each of the microcapsule suspensions prepared in the above Formulation Examples 4 to 6 was adjusted to a predetermined concentration and was sprayed at an amount corresponding to 3,000 L/ha using a fully automatic spraying apparatus (kind of the nozzle and spraying pressure being mentioned later). After the chemical solution was dried (on the day of treatment), a suspension of zoosporangium of tomato late blight (*Phytophthora infestans*) was inoculated by spraying and the tomato was kept in a constant-temperature chamber at 20° C. After 3 days of inoculation, disease index was investigated and disease severity and control value were calculated according to the following expressions. Test results in which spraying was performed using the fully automatic spraying apparatus equipped with Teejet 8001VS nozzle manufactured by Teejet and at a pressure of 40 psi are shown in Table 3 and test results in which spraying was performed using the fully automatic spraying apparatus fitted with Teejet 8003VS nozzle manufactured by Teejet and at a pressure of 30 psi are shown in Table 4.

Disease severity: (1−(the sum of disease index)/4× number of investigated leaves)×100

Control value: (1−(disease severity at each treatment/disease severity at non-treatment))×100

Disease Index (Visual Observation):

0: lesion is not observed at all

1: lesion area is less than 10%

2: lesion area is less than 25%

3: lesion area is less than 50%

4: lesion area is 50% or more

TABLE 3

| Formulation Example | Amount of pesticide active agent Cyazofamid + propamocarb hydrochloride (g/ha) | Disease severity every plastic pot | average | Control value |
|---|---|---|---|---|
| 4 | 60 + 1,000 | 0, 0, 13 | 4 | 96 |
| 5 | 60 + 1,000 | 0, 0, 0 | 0 | 100 |
| 6 | 60 + 1,000 | 0, 0, 0 | 0 | 100 |
| Non-treatment | | 100, 100, 100, 100, 100 | 100 | — |

TABLE 4

| Formulation Example | Amount of pesticide active agent Cyazofamid + propamocarb hydrochloride (g/ha) | Disease severity every plastic pot | average | Control value |
|---|---|---|---|---|
| 4 | 60 + 1,000 | 0, 25, 13 | 13 | 87 |
| 5 | 60 + 1,000 | 0, 0, 0 | 0 | 100 |
| 6 | 60 + 1,000 | 0, 25, 38 | 21 | 79 |
| Non-treatment | | 100, 100, 100, 100, 100 | 100 | — |

Test Example 5

Each of the microcapsule suspensions prepared in the above Formulation Examples 7 and 8 and Comparative Formulation Example 3 was stored in an incubator at 54° C. for 2 weeks. The content of the pesticide active agent before and after the time passage was quantitatively determined by liquid chromatography and the change with time was evaluated in the same manner as in the above Test Example 2. The results are shown in Table 5.

TABLE 5

| Pesticide active agent | Suspension | Decomposition rate (%) |
|---|---|---|
| Nicosulfuron | Formulation Example 7 | 3.00 |
| | Formulation Example 8 | 0.38 |
| | Comparative Formulation Example 3 | 35.00 |

Test Example 6

Each of the microcapsule suspensions prepared in the above Formulation Examples 9 and 10 and Comparative Formulation Examples 4 and 5 was diluted with water and was sprayed from above toward a sample bottle using a hand spray gun (pressure=0.5, 1, 1.5, or 2 psi). After the treatment, the diluted solution was collected from the sample bottle and the state of the microcapsule was observed on a microscope. As a result, the microcapsules of Formulation Examples 9 and 10 were broken under all the pressures, while, in the microcapsules of Comparative Formulation Examples 4 and 5, the shapes thereof were still retained.

Test Example 7

Each of the microcapsule suspensions prepared in the above Formulation Examples 11 and 12 was stored in an incubator at 54° C. for 2 weeks. The content of the pesticide active agent before and after the time passage was quantitatively determined by liquid chromatography and the change with time was evaluated in the same manner as in the above Test Example 2. The results are shown in Table 6.

TABLE 6

| Pesticide active agent | Suspension | Decomposition rate (%) |
|---|---|---|
| Nicosulfuron | Formulation Example 11 | 1.32 |
| | Formulation Example 12 | 0.98 |

Test Example 8

Each of the microcapsule suspensions prepared in the above Formulation Examples 13 to 15 was stored in an incubator at 54° C. for 2 weeks. The content of the pesticide active agent before and after the time passage was quantitatively determined by liquid chromatography and the change with time was evaluated in the same manner as in the above Test Example 2. The results are shown in Table 7.

TABLE 7

| Pesticide active agent | Suspension | Decomposition rate (%) |
|---|---|---|
| Nicosulfuron | Formulation Example 13 | 2.45 |
| | Formulation Example 14 | 4.38 |
| | Formulation Example 15 | 3.59 |

While the present invention has been described in detail and with reference to specific embodiments thereof, it will be apparent to one skilled in the art that various changes and modifications can be made therein without departing from the spirit and scope thereof. The present application is based on Japanese Patent Application No. 2015-102572 filed on May 20, 2015, and the contents are incorporated herein by reference.

The invention claimed is:

1. A microcapsule suspension containing (1) an oil core compound having a pesticide active agent dispersed in an oil compound, (2) an aqueous solution containing a polycationic colloid and a polyanionic colloid in a ratio that the polycationic colloid is from 0.02 to 1% by weight and the polyanionic colloid is from 0.02 to 2% by weight based on the aqueous solution, and (3) a pH adjuster.

2. A microcapsule suspension obtained by covering an oil core compound having a pesticide active agent dispersed in an oil compound with use of an aqueous solution containing a polycationic colloid and a polyanionic colloid in a ratio that the polycationic colloid is from 0.02 to 1% by weight and the polyanionic colloid is from 0.02 to 2% by weight based on the aqueous solution and a pH adjuster to microencapsulate and by suspending the microencapsulated oil core compound in water.

3. The microcapsule suspension according to claim 1 or 2, wherein the blending ratio in the microcapsule suspension is a ratio that the pesticide active agent is from 0.01 to 40 parts by weight, the oil compound is from 0.01 to 50 parts by weight, the polycationic colloid is from 0.01 to 10 parts by weight, the polyanionic colloid is from 0.01 to 10 parts by weight, and water is from 40 to 99 parts by weight.

4. The microcapsule suspension according to claim 1 or 2, wherein pH is from 1.0 to 4.5.

5. The microcapsule suspension according to claim 1 or 2, wherein the oil compound is a vegetable oil or a mineral oil and the whole amount of the pesticide active agent is not dissolved in the oil compound.

6. The microcapsule suspension according to claim 1 or 2, wherein the oil compound is a vegetable oil or a mineral oil and the pesticide active agent is at least one sulfonylurea-based compound selected from the group consisting of nicosulfuron, flazasulfuron, and flucetosulfuron.

7. The microcapsule suspension according to claim 1 or 2, wherein the oil compound is a vegetable oil or a mineral oil and the pesticide active agent is nicosulfuron.

8. The microcapsule suspension according to claim 1 or 2, wherein the oil compound is a vegetable oil or a mineral oil and the pesticide active agent is flazasulfuron.

9. The microcapsule suspension according to claim 1 or 2, wherein the oil compound is a vegetable oil or a mineral oil and the pesticide active agent is cyazofamid.

10. A production method of a microcapsule suspension, comprising:
    (a) a step of mixing a pesticide active agent and an oil compound to prepare an oil dispersion of the pesticide active agent,
    (b) a step of preparing an aqueous solution containing a polycationic colloid and a polyanionic colloid in a ratio that the polycationic colloid is from 0.02 to 1% by weight and the polyanionic colloid is from 0.02 to 2% by weight based on the aqueous solution,
    (c) a step of mixing the oil dispersion and the aqueous solution to form an O/W emulsion, and
    (d) a step of adding a pH adjuster to the O/W emulsion and mixing the whole.

11. The production method according to claim 10, wherein pH is adjusted to from 1.0 to 4.5.

12. The microcapsule suspension according to claim 1, wherein the aqueous solution contains the polycationic colloid and the polyanionic colloid in a ratio that the polycationic colloid is from 0.02-0.7% by weight and the polyanionic colloid is from 0.02-1.4% by weight based on the aqueous solution.

13. A method of releasing a pesticide active component, comprising breaking capsules in the microcapsule suspension according to claim 1 by shear force when stirring the microcapsule suspension in a spray tank or by spray pressure when spraying the microcapsule suspension, to release a pesticide active component.

* * * * *